United States Patent
Helm

(10) Patent No.: US 8,591,446 B2
(45) Date of Patent: Nov. 26, 2013

(54) ORTHO TRAINING DEVICE

(76) Inventor: Dwayne James Helm, Mascotte, FL (US)

(*) Notice: Subject to any disclaimer, the term of this patent is extended or adjusted under 35 U.S.C. 154(b) by 91 days.

(21) Appl. No.: 13/199,562

(22) Filed: Sep. 3, 2011

(65) Prior Publication Data

US 2013/0060180 A1 Mar. 7, 2013

(51) Int. Cl.
*A61F 5/00* (2006.01)

(52) U.S. Cl.
USPC ............................................. 602/23; 602/27

(58) Field of Classification Search
USPC ............... 602/23–28, 60–62; 128/882; 5/624
See application file for complete search history.

(56) References Cited

U.S. PATENT DOCUMENTS

| | | | | |
|---|---|---|---|---|
| 5,368,551 A * | 11/1994 | Zuckerman | 602/23 |
| 5,676,642 A * | 10/1997 | Peters | 602/27 |
| 5,716,335 A * | 2/1998 | Iglesias et al. | 602/27 |
| 5,865,778 A * | 2/1999 | Johnson | 602/27 |
| 6,689,081 B2 * | 2/2004 | Bowman | 602/27 |
| 7,364,561 B1 * | 4/2008 | Morton | 602/27 |
| 7,785,283 B1 * | 8/2010 | Bledsoe | 602/27 |

* cited by examiner

*Primary Examiner* — Michael A. Brown
(74) *Attorney, Agent, or Firm* — Frank B. Arenas, Esq.

(57) ABSTRACT

An article of manufacture, an orthodic device for use with feet and ankles with an arch support removably attached to an ankle brace. A stirrup, tab and tunnel are disclosed.
Optional pads may also be used with versions of the invention.

1 Claim, 8 Drawing Sheets

ORTHO TRAINING DEVICE

CROSS REFERENCE TO RELATED APPLICATIONS

This Nonprovisional application for patent incorporates by reference (to the extent it does not conflict with the disclosure herein) and claims the benefit and priority of pending Provisional application filed 2 Sep. 2011 with US Express Mail #EG 703426560 US entitled "Ortho Training Device" commonly owned with the instant application.

COPYRIGHT NOTICE

A portion of the disclosure of this patent document, including the drawings and Appendices, contain material which is subject to copyright protection. The copyright owner has no objection to the facsimile reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

Versions and embodiments of the present invention relate generally to foot and ankle support devices. Specifically, versions of the invention relate to foot and ankle orthopedic devices that may be quickly changed and adapted to assist in faster healing times, better results and benefits and new, useful and unobvious versions thereof.

2. Description/Background of the Related Art

The art discussed herein is not to be considered admitted prior art but is presented to more clearly discuss and describe what is still lacking in the earlier art.

Foot and ankle orthopedic devices are conventionally made as separate devices. Ankle sprains usually require a bulky device to be worn at all times. Prior art devices must be worn either as an ankle device to support the joint during any and all ambulation or as a foot device for pes planus (flat feet) and/or other foot problems.

When both devices are needed for rehabilitation, one fitting is required for the foot device and another separate fitting is needed for the ankle brace. This second required fitting wastes time for the patient/user/operator/manufacturer. The process of bracing an individual for medial (inside/interior)/lateral (outside/exterior) support is widely known in the industry, but there has not been a device made that would interact with the patient/user in a manner that would serve two functions within the same device.

What is needed is a combined foot/ankle orthopedic device that is more economical to build, lighter, less bulky, cosmetically appealing requires only one fitting and serves two functions within the same device. Versions of this invention solve the at least one, some or all of the above-referenced problems of the prior art and save user time by eliminating the need for two fittings, giving the user of versions of this invention new benefits and results not found in the prior art.

This industry has constant changes and improvements, but nothing of this nature has been developed, introduced, discussed or presented at any level including seminars, trade shows, advertisements, or infomercials is known to this inventor.

The possibilities of versions of this brace/orthotic concept will no longer limit the patient/user to the current option of two separate devices. Not only are the current options very expensive, but typically cumbersome for the user. The current method would require the individual to seek additional support after their injury is healed or they have been released from their physician to resume normal activity. This will involve additional costs and time for manufacturing beyond the initial visit and cost. These additional costs and time spent are saved by this new concept.

No foot and/or ankle device is known to this inventor that addresses the deficiencies in the earlier art as is used in conventional orthopedic devices. This new, useful and unobvious invention and concept, in various embodiments and versions, accomplishes this much needed advantages and unexpected results as compared to conventional orthopedic devices.

SUMMARY OF THE INVENTION

Advantages of versions of the present invention include avoidance and solving of at least one, some, most if not all of the above problems by allowing a combined foot/ankle orthopedic device that requires only one fitting for the patient/user. Orthotics (Greek: Ορθός, ortho, "to straighten" or "align") is a specialty within the medical field concerned with the design, manufacture and application of orthoses. An orthosis (plural: orthoses) is an orthopedic device that supports or corrects the function of a limb or the torso. An orthopaedic brace, "appliance", or simply brace is an orthopaedic device used to:

Control, guide, limit and/or immobilize an extremity, joint or body segment for a particular reason
To restrict movement in a given direction
To assist movement generally
To reduce weight bearing forces for a particular purpose
To aid rehabilitation from fractures after the removal of a cast
To otherwise correct the shape and/or function of the body, to provide easier movement capability or reduce pain Versions of this concept is to incorporate two functional devices into one. This would include a custom foot orthotic with a "tunnel" manufactured in the heel (the tunnel could be partially through the heel or completely through the heel) that would accept a leg brace with a removable plastic "stirrup" with an optional articulating ankle joint which allows free range of motion for ambulation (herein defined as an ortho training device). Versions include optional padding.

The result of versions of this concept would be a functional, lightweight, durable medial/lateral supporting brace with removable uprights/pads that convert to a custom orthotic (arch support) to provide support in times when full bracing is not required. One version of this brace orthotic combination is a "tunnel" in the heel and removable "tab" on the upright support. That results it a unique and dually functional device.

The brace combo may be manufactured as a custom molded device, but can be designed as an "off the shelf" product if desired. This would have tremendous benefits for the general public because of the ankle stabilizing and arch support functions. It would and could be appropriate for anyone that may have an ankle sprain/strain, posterior and anterior dysfunctions, plantar fasciitis, posterior tibia tendon dysfunction (with an additional strapping function), weak ankles, poor ambulation, valgus/varus ankle deformities, and/or pes planus (flat feet).

Versions of this brace have many possibilities. It can be introduced to anyone at any age under almost every possible scenario that involves their feet. Sports, injuries, support, recovery, are all potential uses of versions of the device and benefited by this new concept. The simplicity of the brace and that it will fit into just about any shoe with at least the minimum of a back strap (like a sandal) makes it very versatile and easy to use.

The foregoing objects, benefits and advantages of versions of the invention are illustrative of those which can be addressed by versions of the invention and not intended to be limiting or exhaustive of the possible advantages that can be realized. These and other advantages will be apparent from the description herein or can be learned from practicing versions of the invention, both as embodied herein as examples or as modified in view of any variations which may be apparent to those of ordinary skill in the art. Therefore, the invention resides in the novel devices, methods, arrangements, systems, combinations and improvements herein shown and described as examples and not limited therein.

BRIEF DESCRIPTION OF THE DRAWINGS

In the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

Figure 1:
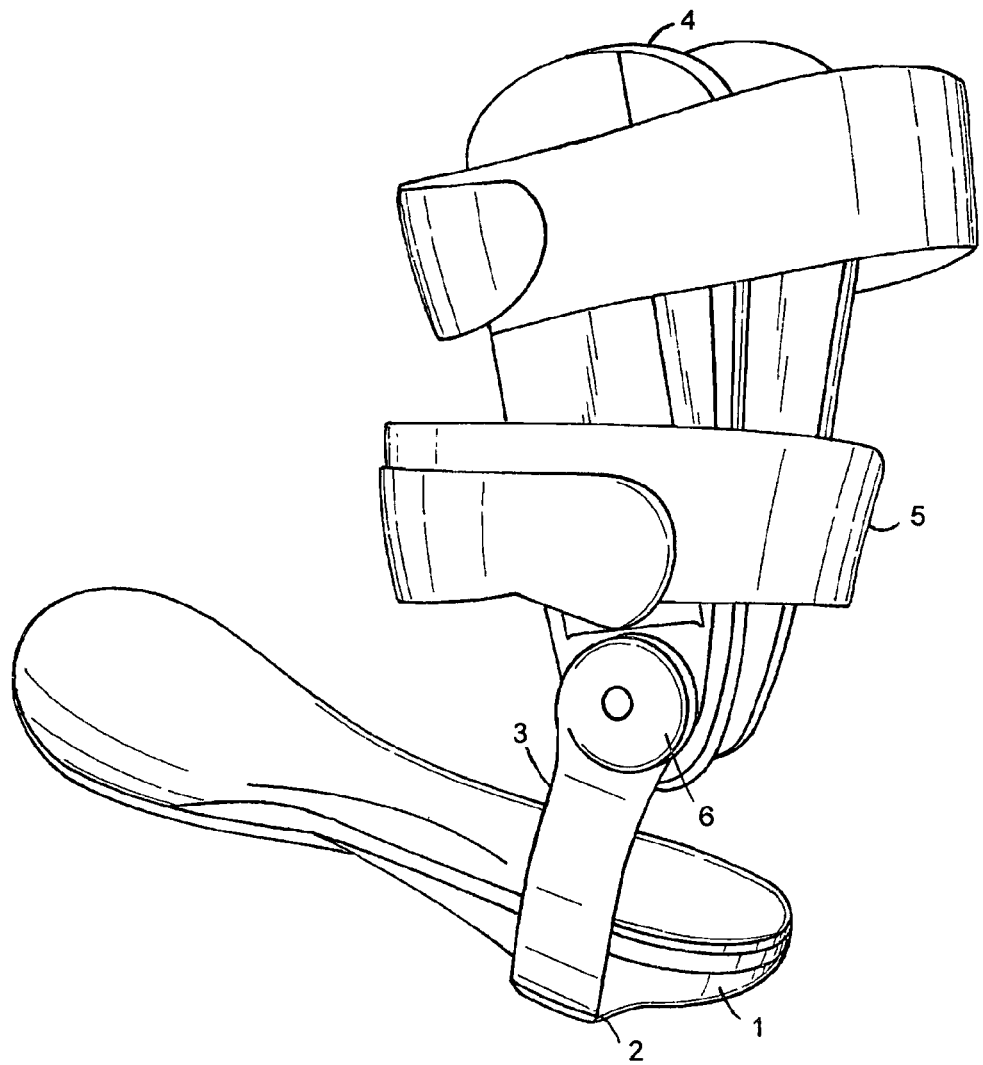
FIG. 1 is a perspective view of an embodiment of a version of the invention.
Figure 2:
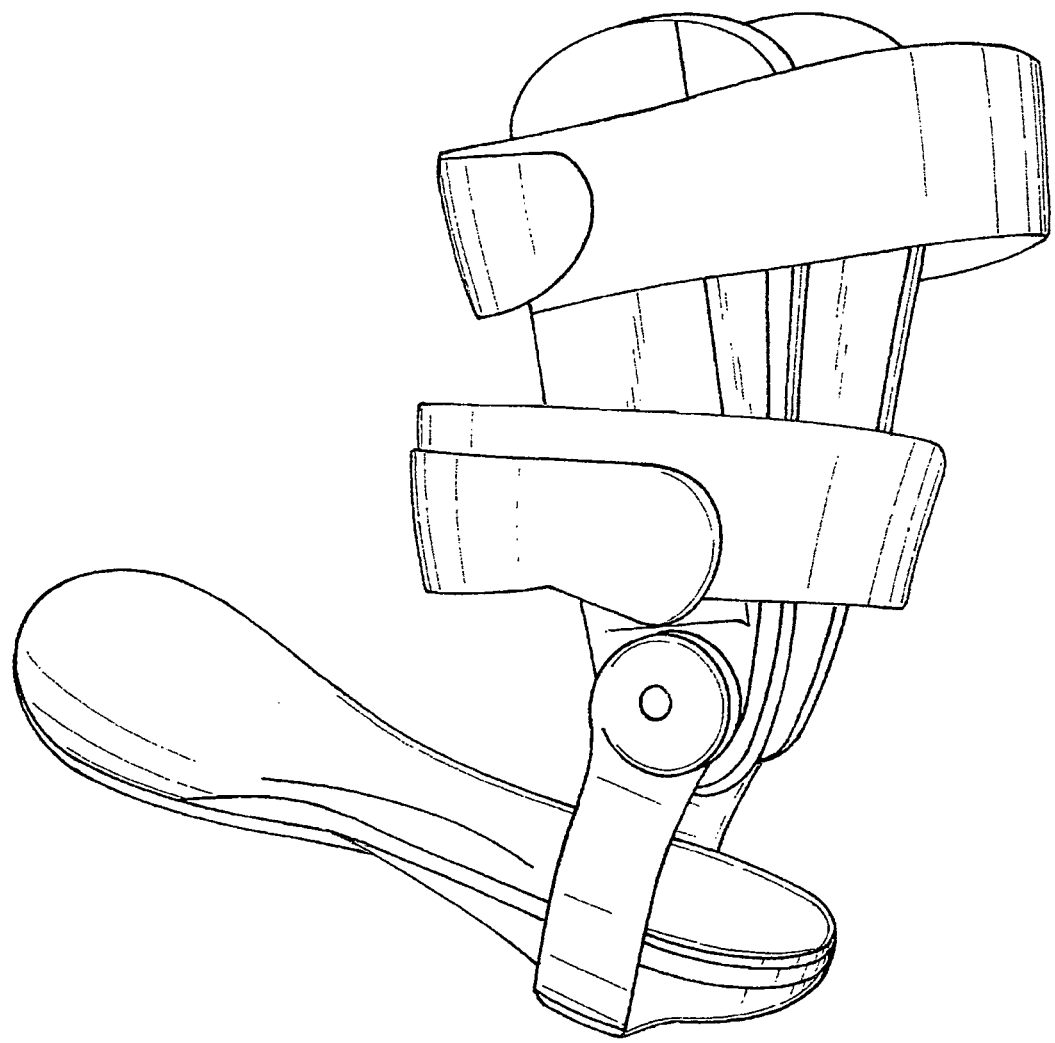
FIG. 2 is a perspective view of a preferred embodiment of a version of the invention.
Figure 3:
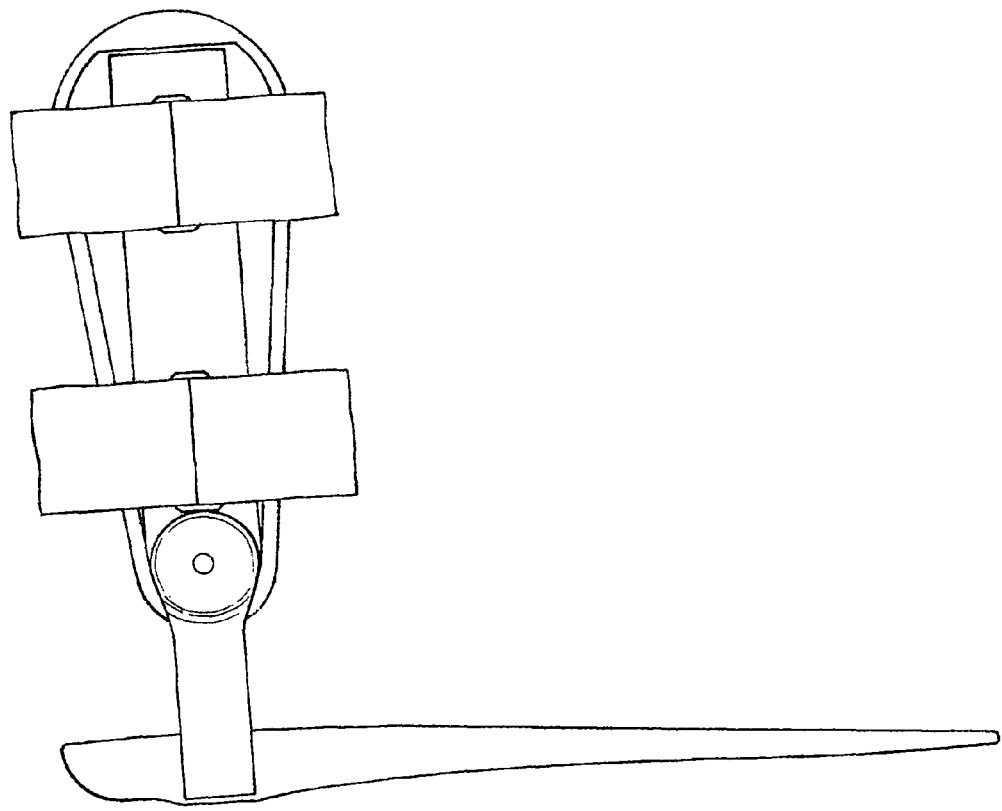
FIG. 3 is a side view of a version of the invention.
Figure 4:
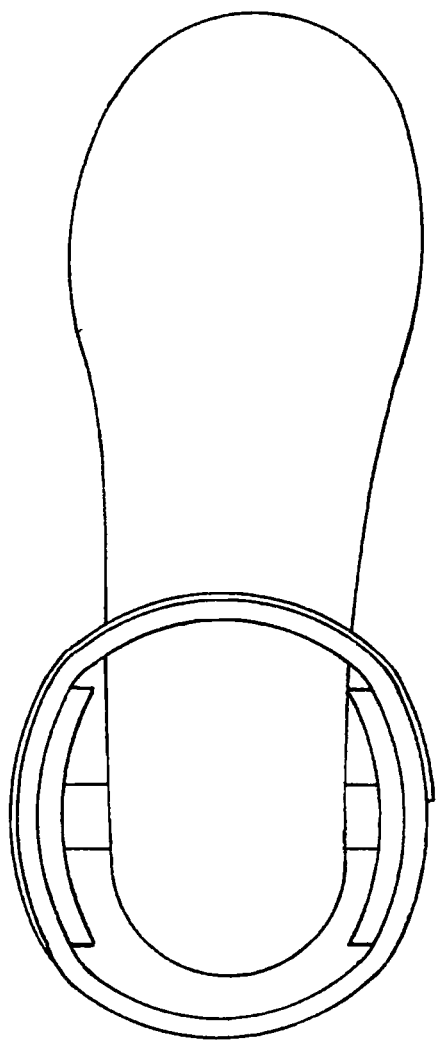
FIG. 4 is a top view of a version of the invention.
Figure 5:
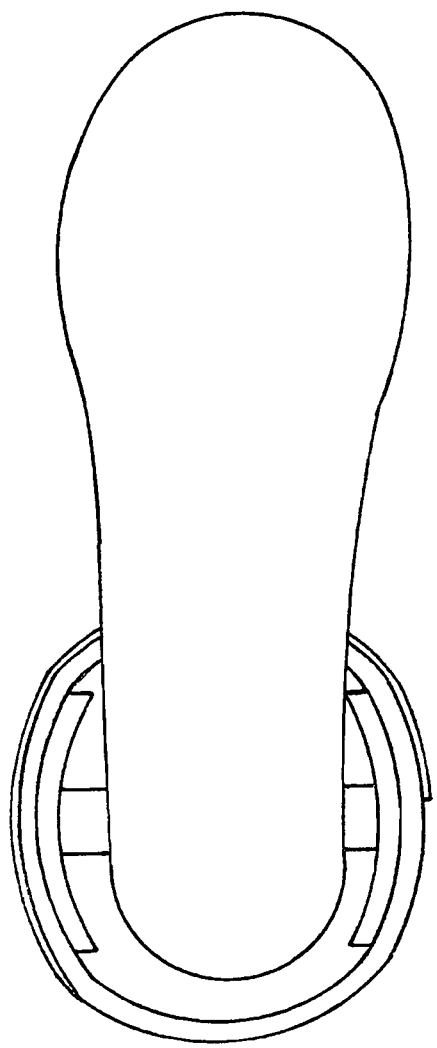
FIG. 5 is a bottom view of a version of the invention.
Figure 6:
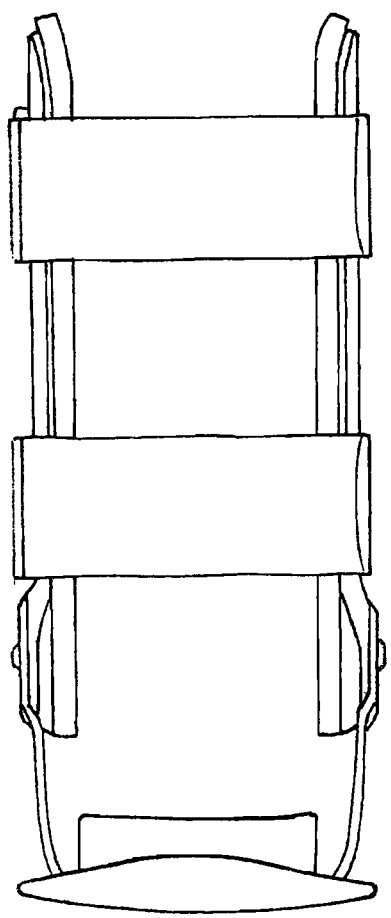
FIG. 6 is a front view of a version of the invention.
Figure 7:
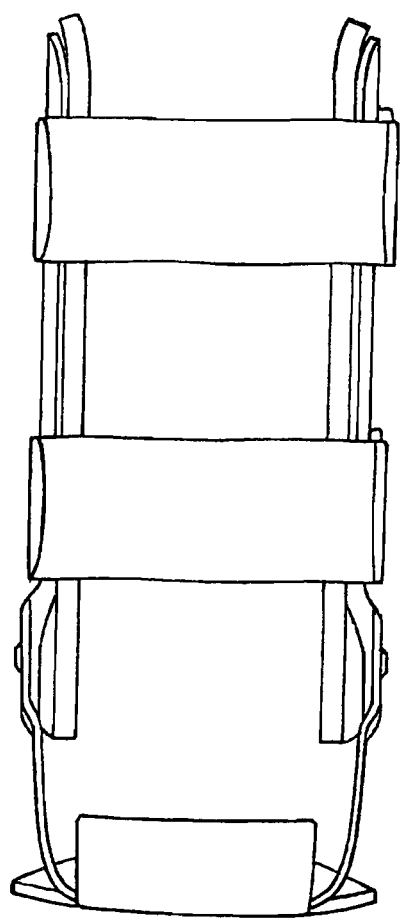
FIG. 7 is back view of a version of the invention.

While the present invention will be described with reference to the details of the embodiments of the invention shown in the drawings (and some embodiments not shown in the drawings), these details are not intended to limit the scope of the invention. As would be known by one of average skill in the art, such as a foot/ankle orthopedic designer/builder, orthopedic doctor or similar individuals, modifications may be made that are intended to be within the scope of versions of the invention.

DETAILED DESCRIPTION OF A PREFERRED EMBODIMENT

It is also understood that whenever and/or is used in this patent application it means any combination or permutation of all, one, some, a plurality or none of each of the item or list mentioned, which is not intended to be limiting but merely for example and illustration. It is also understood that (s) designates either singular or plural. It is also understood that "or" is an inclusive "or" to include all items in a list and not intended to be limiting and means any combination or permutation of all, one, some, a plurality or none of each of the item or list mentioned. It is also understood that "include(s)" and/or "including" means "including but not limited to" any combination or permutation of all, one, some, a plurality or none of each of the item or list mentioned.

The core of the version of the basic embodiment of the invention is depicted in FIG. 1. The basic component is at least one base 1, which may be any suitable shape but illustrated herein as a orthodic (orthopedic) arch support of suitable length, width and height fabricated such that at least one base attachment 2 (attachment means or means for attaching) is integrated into at least one axis of the base 1. The base can be made to approximate a foot outline and about one-eighth inch thick in one layer or use a plurality of layers. The base could also be custom made from computer-aided foot standing pressure analysis devices commonly known in the art. The base may be used alone or as an insert in a shoe worn by the operator. The base attachment 2 ("tunnel" in some versions) and at least one vertical brace 3 ("stirrup" in some versions) are shaped such that the vertical brace ("tab" in some versions) may be removably attached to the base attachment and released if desired. The vertical brace 3 is made of any suitable material, metal and/or rubber and/or pliable plastic. At least one vertical brace leg attachment (attachment means or means for attaching) means 5 is disposed onto or into the vertical brace 3.

Optional components are interior pad(s) 4 (means for padding) and vertical brace ankle pivot(s) 6 (means for pivoting).

The components may be attached, connected, linked, related, affixed, disposed on, integrated into, adjoined, combined, bonded, united, associated, joined, tied, secured, bound, releasably attached, rigidly attached, flexibly attached, attached with rotational freedom in at one least axis, and/or integrated into or onto each other as desired by the operator or manufacturer.

The attachment means may be of any suitable type—loop, aperture, glue, sewn, webbing, fastener, screw, bolt, wingnut, weld, connector link, grommet, snap, rivet, thread, rope, twine, rod, dowel, hook, plug, connector, touch fastener (Velcro—trademarked), tunnel, tab, stirrup and/or any other means, either attached/secured permanently, temporarily and/or releasably attached.

At least one of the basic components is necessary but a plurality may be utilized if desired for different versions of the invention. This great improvement over the prior art expands greatly the operator's control of both the ankle brace and arch support base, producing new results and reducing the fitting time of conventional arch support(s) and ankle braces when used. This saves money by allowing the ankle to heal, then remove the vertical brace and keep the arch support which reduces two patient/user fittings to one fitting only. Versions include the base and vertical brace able to be attached or detached manually without tools by the operator.

Versions of the invention may be made with any and all suitable materials desired as needed for the appropriate use and is not limited by the type of materials that may be used. Versions are all scalable and may be made any suitable size; large, small and/or any size as desired.

A preferred embodiment uses plastics and/or plastic injection molding techniques and/or plastic vacuum molding techniques, well know in the art. These non-metallic materials include, among others, conventional polymers such as, for example, foam padding, polystyrene, polycarbonate, polyurethane, polyethylene, phenol formaldehyde resins, polybutylene, Teflon and the like.

Versions of the device may be made of biodegradable materials to allow the device to be disposable in a "green" manner and/or recycled.

All components may be referenced in plural for convenience, as only at least one of all components are necessary, if desired, for proper operation and use in other embodiments. Ideally, all components (or some components) are injection molded from non-metallic materials (plastic and/or rubber, including natural and/or synthetic rubber and/or rubber-like compositions) foam padding, or vacuum molded as previously mentioned above.

To make the invention in a basic embodiment, one skilled in the art would follow these steps (for illustration only and not intended to be limiting) but are not solely limited to these instructions. Some materials or processes may be changed to accommodate a custom device. These fabrication steps are well known in the industry.

Foot Plate/Orthotic (Base):
1) Take cast of foot/feet (or use foot impression block).
2) Fill cast (or impression block) with Plaster of Paris making a positive cast.
3) Remove negative casting material around mold.
4) Make modifications to cast as indicated for patient use.
5) Heat material that will be used for suction forming such as thermoplastic or carbon, etc. . . . One piece ⅛" heel to mid foot, then add ⅛" metal plate to form tunnel across heel. Place second piece of ⅛" over entire cast.
6) Vacuum form material to mold.
7) Allow to cool.
8) Mark trim lines and cut/smooth foot plate to desired shape.
9) Top of orthotic may have a foam, ppt, plastizote, poron, spenco, etc. added for desired cushion cut to desired length (may be ¾ or full foot). Glue material after cutting plate and finish with vinyl or similar material for finished look.

Upright(s) (Vertical Support):
1) Use a 2×4 block of wood and make a 1" pilot hole at one end of the 2×4.
2) Cut a ¾" (outer diameter) by 12" (in length) PVC pipe and glue into the hole made in the wood.
3) Use a 1" hole saw and 3/16" piece of plastic to make disc for ankle joint.
4) Remove plastic from hole saw, deburr and smooth (make 4 discs).
5) Wrap a 1×4 with 1/16" puff or firm foam and glue with spray adhesive like Spray 77 to adhere foam to wood block.
6) Set ankle discs on top of foam.
7) Heat 3/16" plastic by convectional or infrared oven to allow for vacuum forming over 2×4 wood.
8) Allow to cool, and then use cast saw or similar equipment to cut out stirrup that is 1"×5" in length.
9) Smooth and deburr edges.
10) In center ankle, make a hole with a ¼" drill bit.
11) Measure from center hole down to 3" and make horizontal line.
12) Use a heat gun or torch to heat material and bend angle to 90 degrees.
13) Take another joint from center of hole to 2½" and follow heat and bend instructions as in #12.
14) Take both pieces from bend to horizontal end of piece and mark 1". Cut excess and smooth and deburr. This will now create the "tab" like function of the stirrup.
15) Use 4" water pipe with one end capped and fill the inside drum with Plaster of Paris.
16) Cut 12" by ¾" PVC pipe and place inside center of plaster before setting jig (do not remove plaster from PVC pipe)
17) Wrap with foam like in #5 and glue.
18) Take 1" ankle templates and glue to foam 1" from cylinder top down.
19) Cut ⅛" T×16" W×24" L plastic
20) Heat and vacuum form plastic to cylinder.
21) Deburr and smooth upright.
22) Use rivets or similar to add uprights to split stirrup.

Padding (Optional):
1) 3/16" soft accommodative foam such as ppt, plastizote, or equivalent should be cut to shape of upright.
2) Cut two pieces equally using vinyl, leather, etc., to create an outer covering over the 3/16" foam pieces.
3) Glue together with foam on inside.
4) Cut remaining cover leaving a 1" welt around outer edge.
5) Cut 2 pieces of self-adhesive touch fastener hook to length of pad.
6) Pull adhesive backing off and adhere to pad.
7) Cut 4 pieces of self-adhesive touch fastener hook to length of upright and add on one piece to inside and one piece to outside of the upright in a vertical manner.
8) Add 2-20" touch fastener straps to wrap around proximal and distal uprights in a circumference form.
9) Brace is complete, subject to customization.

Follow these instructions for each brace, making adjustments as needed. The stirrup should be attached to the tunnel by placing tabs inside the tunnel securely in a preferred embodiment. When use of only the foot arch support base is desired, the patient/user does not attach (or detaches) the stirrup tabs from the tunnel.

The primary requirements for successful use of versions of the invention are the design parameters set by the size and/or shape of the patient/user and size of foot, ankle and calve. These requirements may vary from one patient to another.

Figure 8:
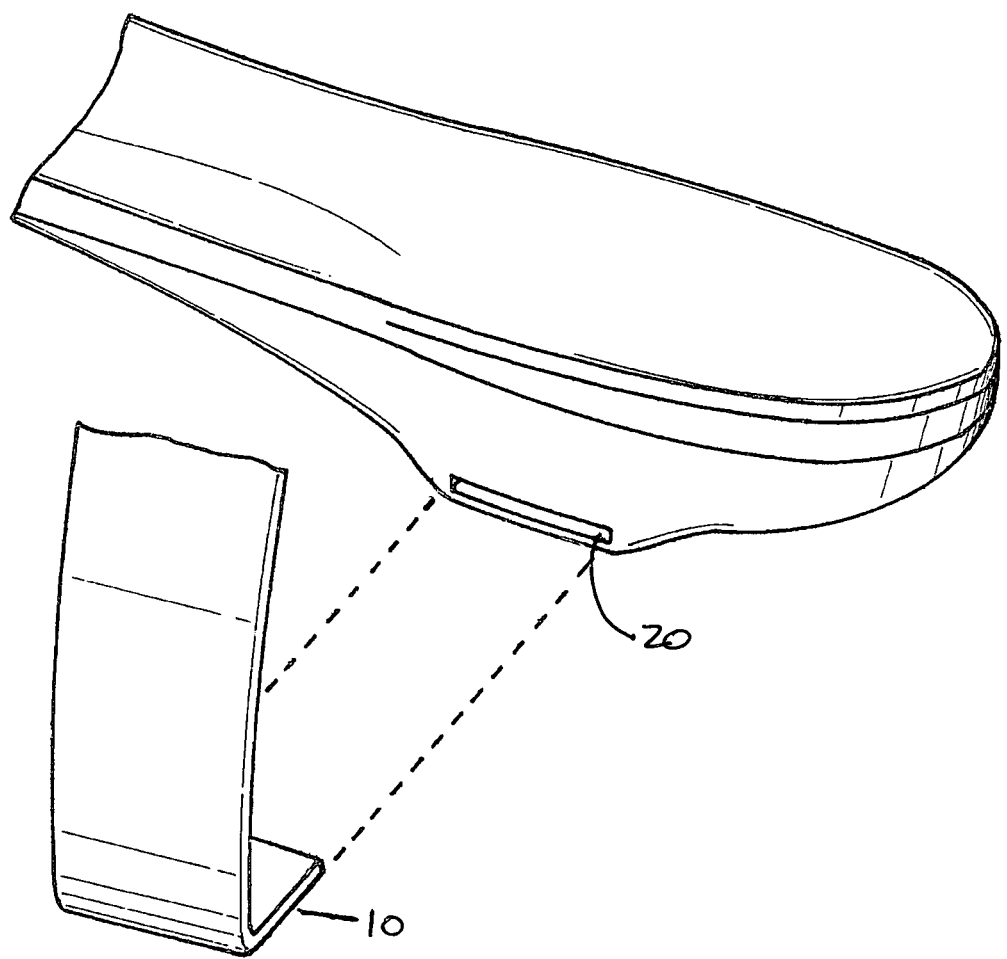
FIG. 8 is a perspective detail view of the tab and tunnel in attach/detach modes used in alternate embodiments of the invention.

To use the invention in this embodiment, the patient/user would step into the device with the stirrups attached, aligning the foot centered over the weight bearing arch support and wrap the straps around the calve. Then the patient/user puts her foot with the device into her shoe (or other suitable foot covering) and laces the shoe normally. To take off the device, this procedure is reversed. If only the foot arch support base is desired, the patient/user detaches the stirrup tab(s) 10 from the tunnel 20 (as depicted in FIG. 8) and inserts the arch support into the desired shoe, then puts her foot in the shoe. The attachment/detachment means could also include no requirement for tools, but done completely by hand. The tunnel and tab(s) may be friction fit.

A plurality of layers can be used with elastic, plastic and/or metallic layer(s) in any combination as desired by the user (or operator or manufacturer) with any suitable material(s). For example, the arch support base could made in layers to match the contour of the user/patient's foot, using different density of foam layers. The vertical brace pads could also be made in layers of different densities of foam. And the vertical uprights themselves could be made in layers (laminated) to achieve a desired stiffness. Malleable metal also may be used in versions of the invention, alone or in combination with other materials.

The above-referenced list(s), option(s), function(s), instruction(s), component(s), application(s), interaction(s), item(s), product(s), good(s), group(s) and sub-group(s) are merely intended as illustration and examples, and are not intended by the inventor to in any way limit the addition, deletion or modification of any said list(s), option(s), function(s), instruction(s), component(s), application(s), interaction(s), item(s), product(s), good(s), group(s) and sub-group(s) as might be desirable or useful to someone skilled in the art.

As will be apparent to persons skilled in the art, such as a person in the arch support designer/manufacturer and/or ankle brace designer/manufacturer and/or orthodic designer or other similar-type individuals, various modifications and adaptations of the structure and method of use above-described will become readily apparent without departure from the spirit and scope of the invention, the scope of which is defined in the claims. Although the foregoing invention has been described in detail by way of illustration and example, it will be understood that the present invention is not limited to the particular description and specific embodiments described but may comprise any combination of the above elements and variations thereof, many of which will be obvious to those skilled in the art. Additionally, the acts and actions of fabricating, assembling, using, and maintaining the preferred embodiment of this invention is well known by those skilled in the art. The invention may be embodied in other specific forms without departing from the spirit or essential characteristics thereof. The present embodiment is therefore to be considered in all respects as illustrative and not restrictive, the scope of the invention being indicated by the claims rather than by the foregoing description, and all changes which come within the meaning and range of equivalency of the claims are therefore intended to be embraced therein.

I claim:

1. An article of manufacture, an ortho training device for use with a foot and ankle inside a shoe, comprising:

A custom made foot orthotic of a suitable length, width and height, further comprising a tunnel integrated into a heel of the foot custom made orthotic and;

further comprising a stirrup of a suitable length, width and height with a top end and a bottom end, further comprising a tab on the bottom end, said stirrup releasably attached to the heel of the foot orthotic via the tab on the bottom end of the stirrup pushed into the tunnel integrated into the heel of the custom made foot orthotic with a friction fit, and;

further comprising a strap disposed on the stirrup top end, and;

further comprising a pad disposed on the stirrup top end, wherein the custom made foot orthotic may be released from the stirrup via the tab and tunnel integrated into the heel of the custom made foot orthotic and used alone inside a shoe by the operator.

* * * * *